United States Patent
Zheng et al.

[11] Patent Number: 5,997,540
[45] Date of Patent: *Dec. 7, 1999

[54] HIGH EFFICIENCY EXTERNAL COUNTERPULSATION APPARATUS AND METHOD FOR CONTROLLING SAME

[75] Inventors: Zhensheng Zheng; Zhili Huang; Shifang Yang; Ying Liao, all of Guangzhou, China

[73] Assignee: Vasomedical, Inc., Westbury, N.Y.

[*] Notice: This patent is subject to a terminal disclaimer.

[21] Appl. No.: 08/955,421

[22] Filed: Oct. 22, 1997

Related U.S. Application Data

[63] Continuation of application No. 08/711,129, Sep. 9, 1996, abandoned, which is a continuation of application No. 08/396,261, Feb. 27, 1995, Pat. No. 5,554,103, which is a continuation of application No. 08/058,394, May 6, 1993, abandoned.

[30] Foreign Application Priority Data

| May 7, 1992 | [CN] | China | 92103545 |
| May 8, 1992 | [CN] | China | 92209589 |
| May 8, 1992 | [CN] | China | 92209813 |

[51] Int. Cl.⁶ ......................................................... A61B 5/00
[52] U.S. Cl. ............................ 606/64; 601/152; 600/311
[58] Field of Search ................... 606/201, 64; 601/152; 128/64, 672, 691–693, 677

[56] References Cited

U.S. PATENT DOCUMENTS

| 3,862,629 | 1/1975 | Rotta | 128/64 |
| 4,077,402 | 3/1978 | Benjamin, Jr. et al. | 128/64 |
| 4,253,449 | 3/1981 | Arkams et al. | 128/64 |
| 5,000,164 | 3/1991 | Cooper | 128/64 |
| 5,554,103 | 9/1996 | Zheng et al. | 601/152 |

*Primary Examiner*—Michael Buiz
*Assistant Examiner*—Kevin Truong
*Attorney, Agent, or Firm*—Majestic, Parsons, Siebert & Hsue P.C.

[57] ABSTRACT

The present invention provides a high efficiency external counterpulsation apparatus having accurate and reliable timing of inflation and deflation and reduced temperature of the pressurized gas, such that the gas flow temperature of the balloons is near to room temperature. The external counterpulsation apparatus also has a new gas distribution device and devices for monitoring the blood pressure and oxygen levels in the blood of a patient for improving safety. The present invention further provides a method for controlling the external counterpulsation apparatus.

24 Claims, 9 Drawing Sheets

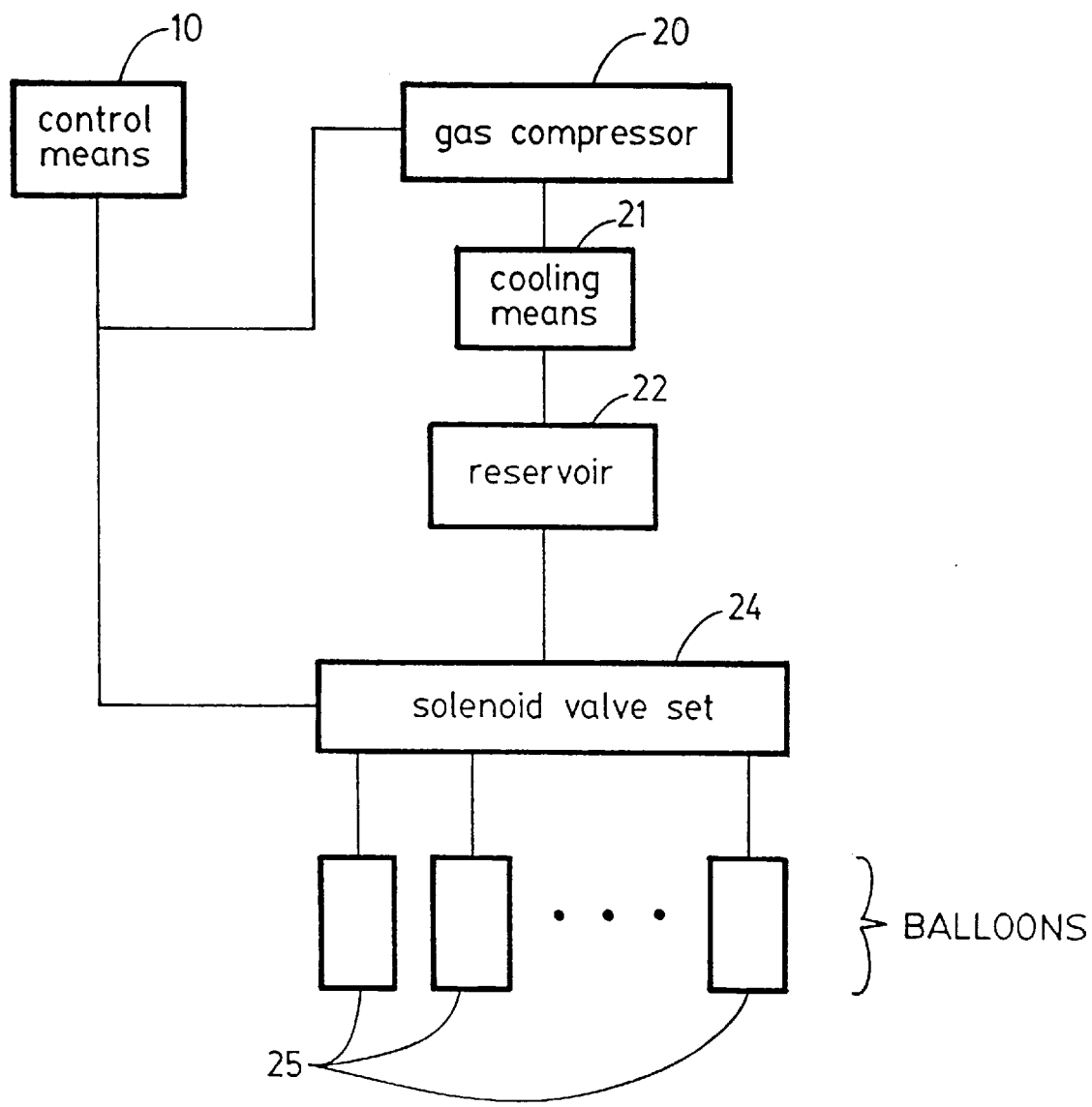
FIG._1.

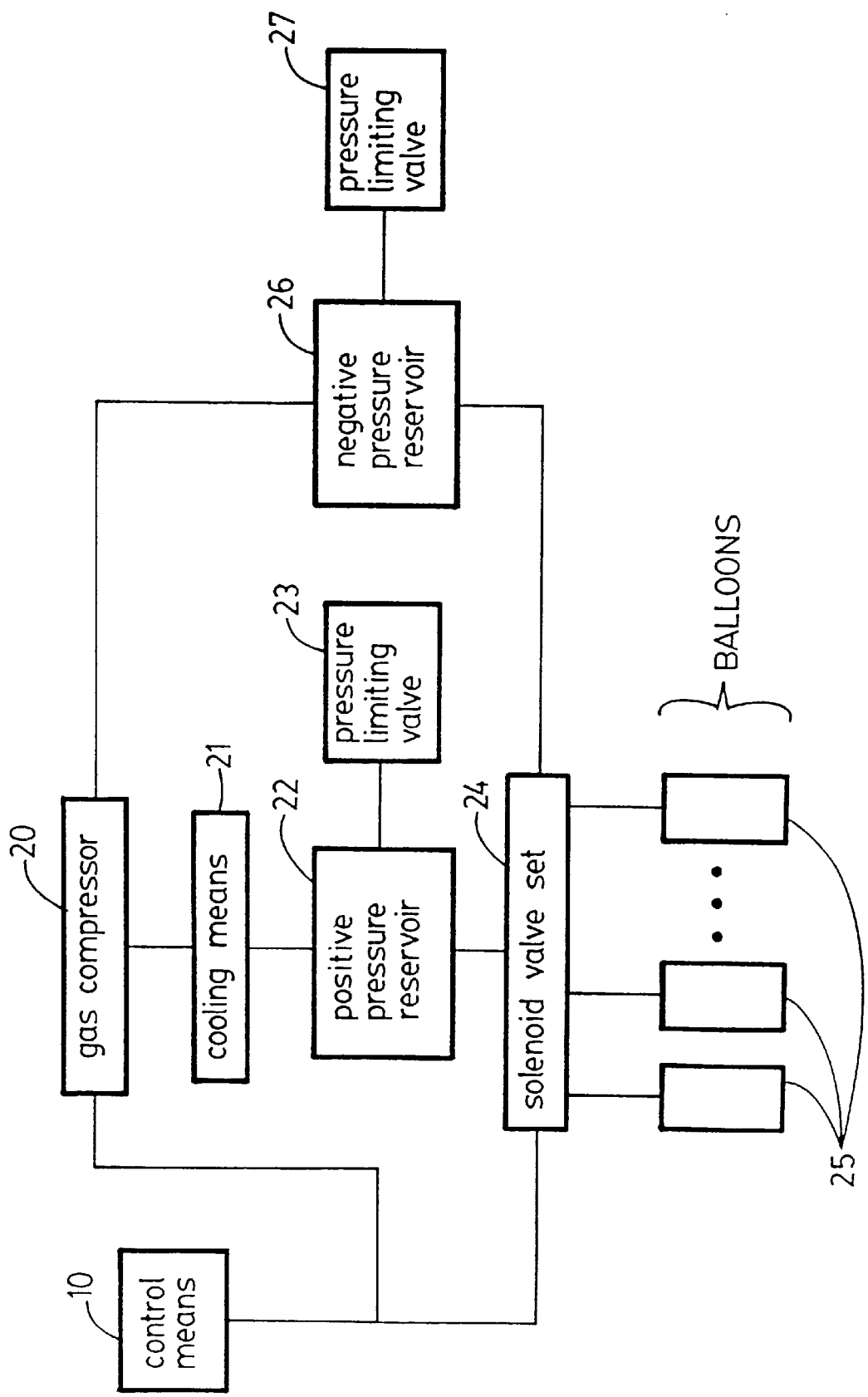
FIG._2.

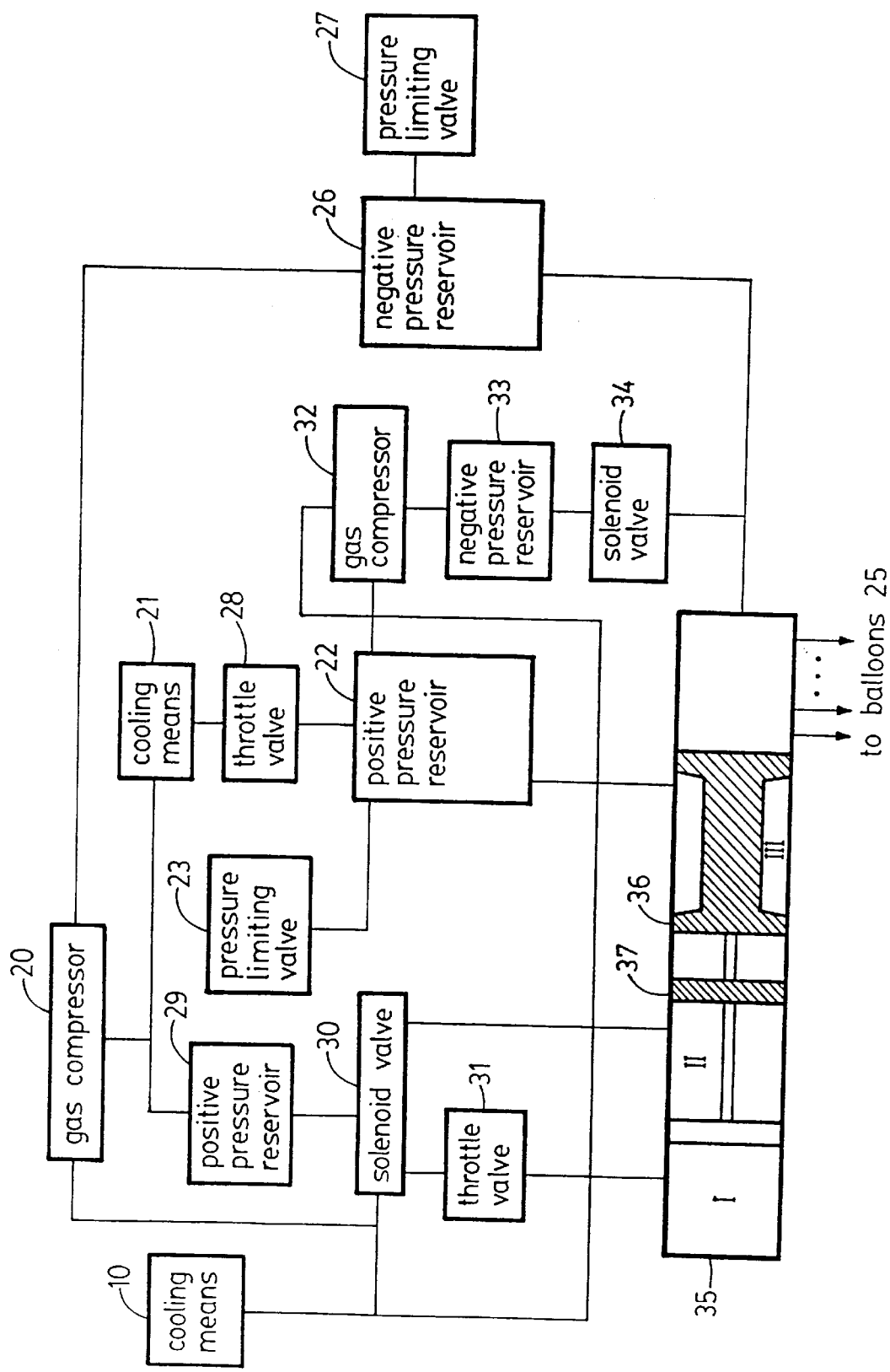
FIG._3.

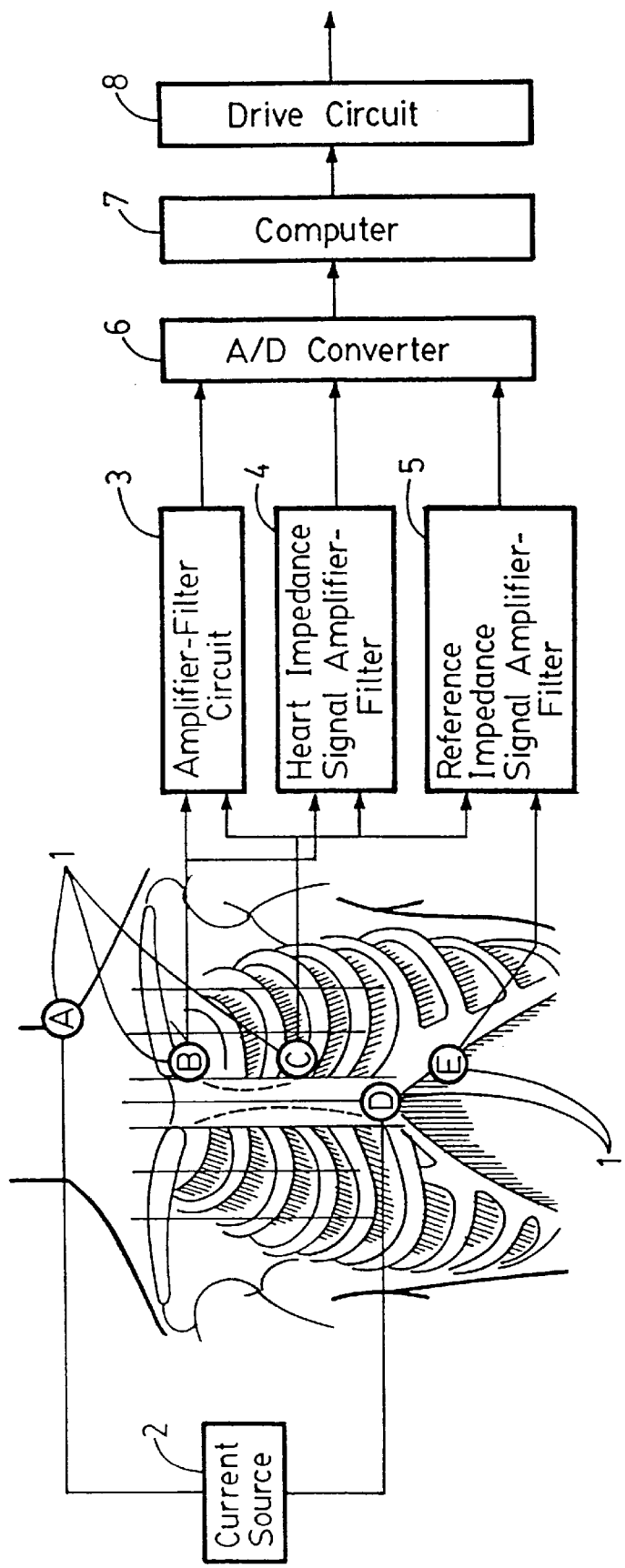
FIG._4A.

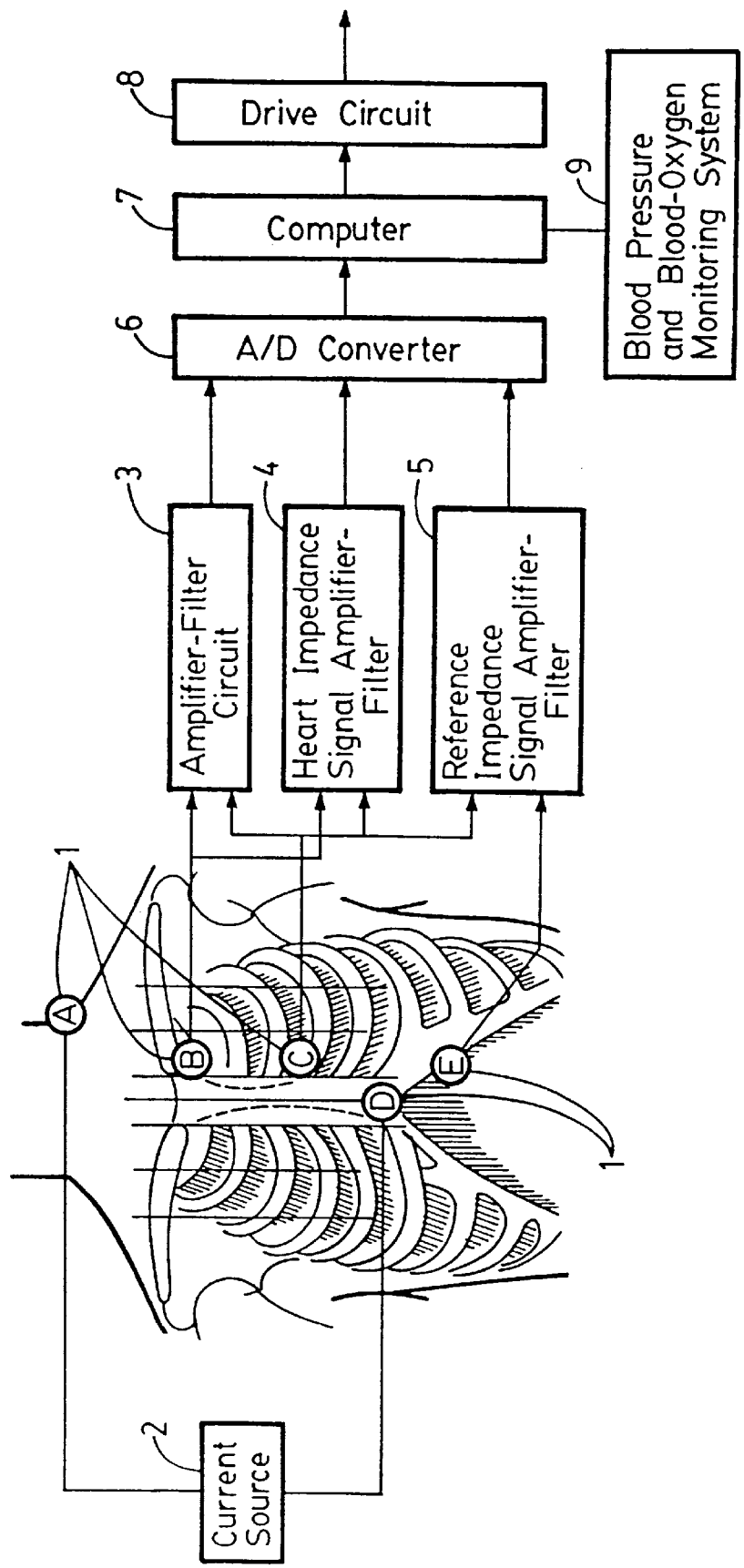
FIG._4B.

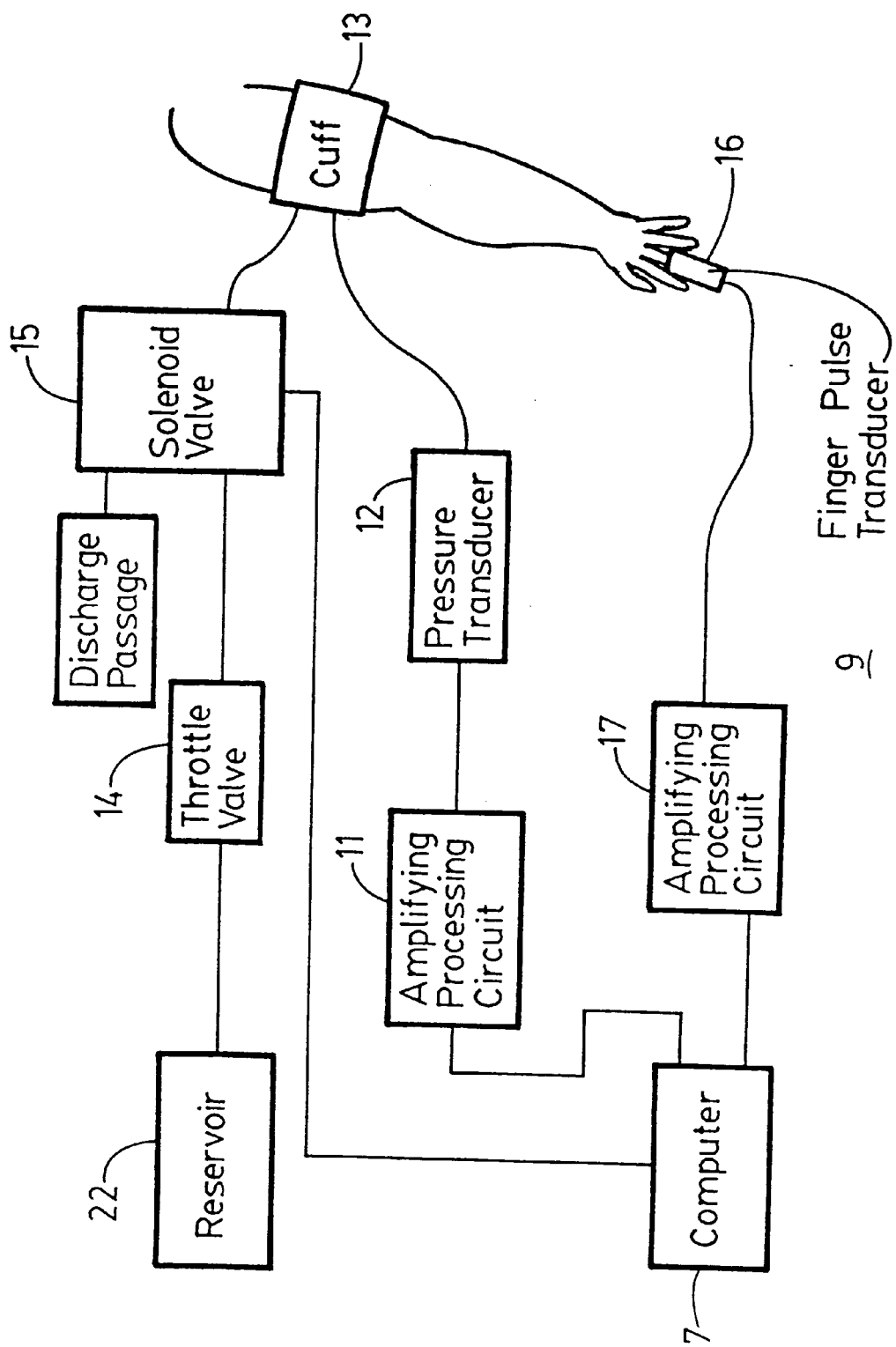
FIG._4C.

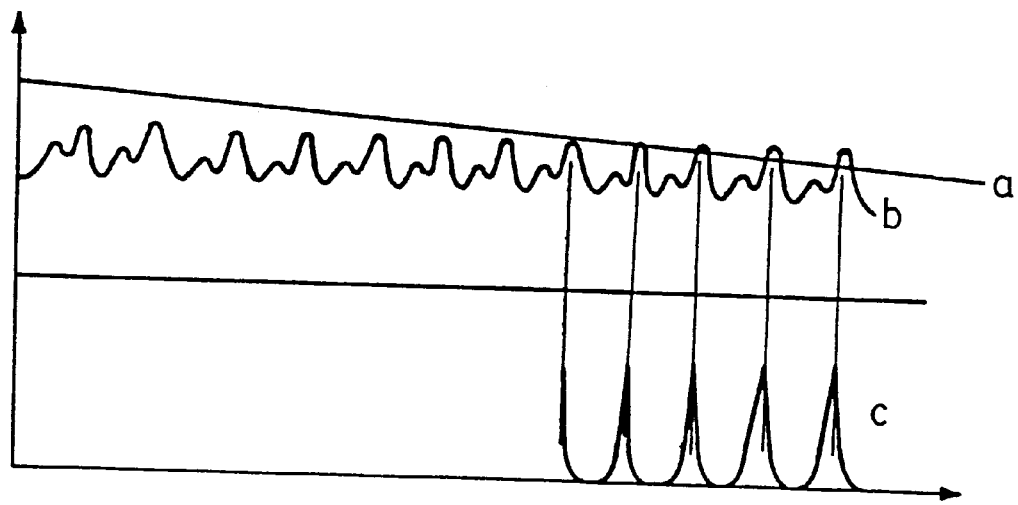
FIG._4D.
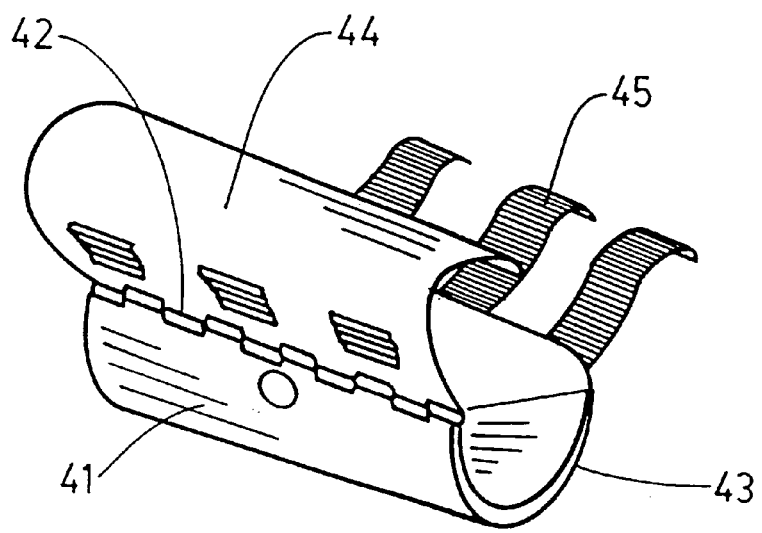
FIG._6.

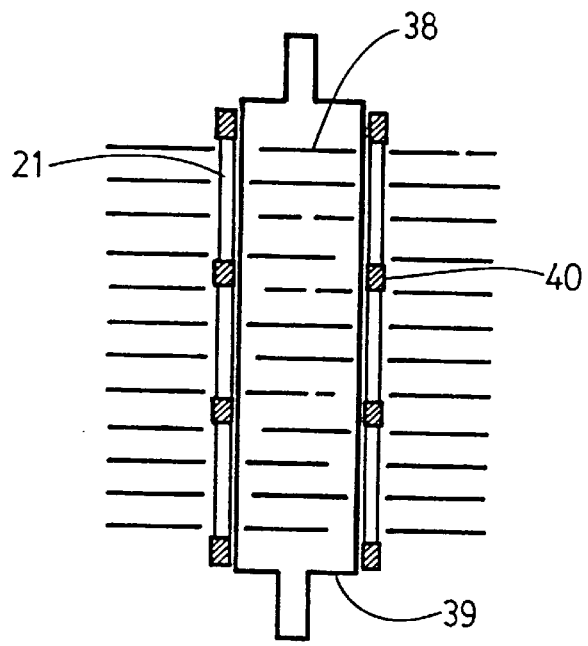
FIG._5A.
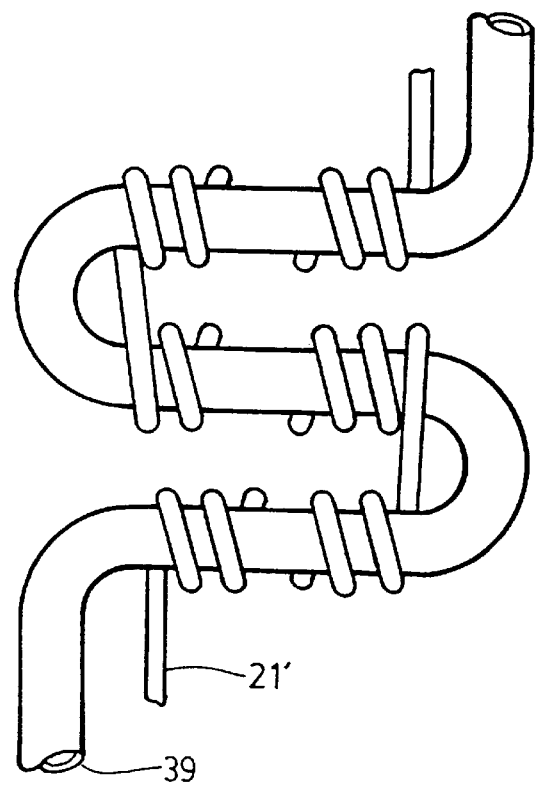
FIG._5B.

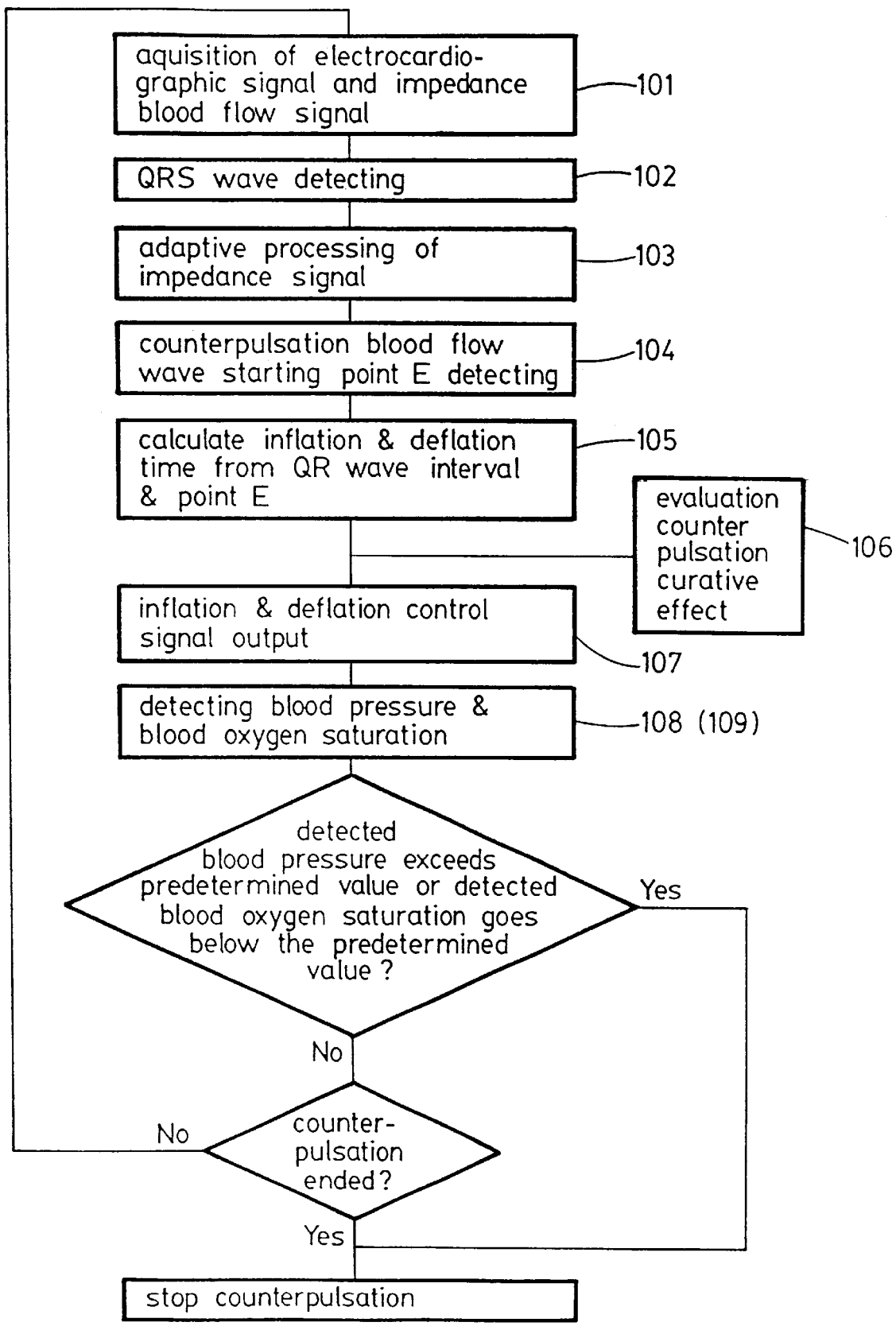
FIG._7.

HIGH EFFICIENCY EXTERNAL COUNTERPULSATION APPARATUS AND METHOD FOR CONTROLLING SAME

This is a continuation of U.S. patent application Ser. No. 08/711,129, filed Sep. 9, 1996 now abandoned, which is a continuation of U.S. application Ser. No. 08/396,261, filed Feb. 27, 1995, now U.S. Pat. No. 5,554,103, which is a continuation of U.S. patent application Ser. No. 08/058,394, filed May 6, 1993, now abandoned.

FIELD OF THE INVENTION

The present invention relates to an external counterpulsation apparatus and method for controlling the same, more particularly, to an improved efficiency external counterpulsation apparatus and method for controlling the same.

BACKGROUND OF THE INVENTION

External conterpulsation provides tangible curative effect in the treatment of cardiovascular diseases, which have become more and more prevalent in recent years. In American Cardiovascular Journal (30(10)656–661, 1973) Dr. Cohen reported a device for external counterpulsation, being a four—limb sequential counterpulsation device. It consists of multiple balloons wrapped around the four limbs of the patient. Pressure is applied sequentially from the distal to the proximal portion of each limb. Using high pressure gas from a large compressor as its energy source (1000 to 1750 mm Hg) to control the opening time of a solenoid valve, the balloons receive pressurized air during inflation. The balloons are deflated by use of a vacuum pump. The device requires the use of a large air compressor, a large vacuum pump and the use of numerous pressure transducers to monitor the input pressure to insure that no excessive pressure is exerted in the balloons. However, this device is not only, bulky and expensive, but it is also extremely noisy and, complicated to operate. It is, therefore, unsuitable for everyday clinical use.

External cardiac assistance has been described in U.S. Pat. No. 3,866,604, which is an improvement on the above original external counterpulsation device. However, this device is extremely bulky, noisy, and complicated to operate.

An external counterpulsation apparatus has also been described in Chinese Patent CN85200905, which has been granted by U.S. Pat. No. 4,753,226. This external counterpulsation apparatus is regarded as another improvement over previous art. In addition to balloons for the four limbs, it also comprises a pair of buttock balloons. The balloons are sequentially inflated with positive pressure and then, with appropriate delay, simultaneously deflated using a microcomputer to control the opening and closing of solenoid valves. The high pressure gas source and vacuum pump have been eliminated, so as to reduce the volume of the apparatus and make it more practical. However, the deflation of the balloons of this apparatus lacks the suction of negative pressure and depends on natural exhaustion into the atmosphere. Therefore, the exhaustion of the balloons is incomplete and slow, and leaves behind residual gas in the balloon which hinders the ability of this device to reduce after load (workload) of the heart.

A positive and negative enhanced type external counterpulsation apparatus has been described in Chinese Patent CN88203328, wherein a negative pressure suction means for exhaustion of the balloons has been added. However, this apparatus is still ineffective in the exhaustion of all the pressurized gas in the balloons and in addition, it is still too large, noisy and heavy for transport to be of practical application in the clinical setting.

A miniaturized external counterpulsation apparatus has been described in Chinese Patent CN1057189A, wherein the air compressor can be placed inside the main body of the device and does not require a separate embodiment. The box containing the solenoid valves and the balloon cuffs are suspended in a tube like apparatus and directly attached to the main body of the device. This device is practical for clinical use in that its size is very much reduced. However, this device does not have negative suction to increase the rate of deflation of the balloons, and it is still extremely noisy and not very efficient in producing desirable counterpulsation hemodynamic effects, namely, a high rate of inflation and effective deflation.

The foregoing external counterpulsation apparatuses have many advantages over the original one, but there are still many problems. For example, the high pressure air produced by the air compressor has a high temperature when it arrives at the balloons, which may cause Feeling of Discomfort or even pain for the patient; the balloon cuff used by the prior art external counterpulsation apparatus is made of soft materials such as leatherette, canvas and the like, which may have a high elasticity and extensibility, requiring the use of a large volume of gas to achieve the required pressure and resulting in the inability to quickly inflate the balloons for optimal rate of inflation. Furthermore, dead space may be formed due to the misfit between the balloon cuff and the surrounded limb; the balloon cuff could slip downward during counterpulsing thereby being incapable of efficiently driving blood from peripheral regions to the root of the aorta, which directly affects the effectiveness of the counterpulsation treatment. All these factors reduce the efficiency of counterpulsation and require more pressurized gas to fill up dead space and more power from the compressor. At the same time a reduction in the rate of inflation of the balloon results in hindering the effective compression of the body mass as well as vasculature.

Historically, the earlobe pulse wave, finger pulse or temporal pulse wave are used in a timing signal to give the appropriate time for application of the external pressure so that the resulting pulse produced by external pressure in the artery would arrive at the root of the aorta just at the closure of the aortic valve. Thus the arterial pulse wave is divided into a systolic period and a diastolic period. However, earlobe pulse wave, finger pulse wave or temporal pulse wave are signals derived from microcirculation and may not reflect the true pulse wave from the great arteries such as the aorta. Using the dicrotic notch as the true aortic valve closure is incorrect because the dicrotic notch is affected by many other factors such as the dampening effect of the vascular elasticity, reflective wave from tapering of the arteries and interference from previous pulse waves. Therefore, it is most important in the art of external counterpulsation to find the true aortic valve closure time so the appropriate inflation time can be found for the externally applied pressure.

Theoretically, there are two factors that should be taken into account to determine the appropriate deflation time of all the balloons simultaneously. (1) release of all external pressure before the next systole to produce maximal systolic unloading, that is the maximum reduction of systolic pressure; (2) maintenance of the inflation as long as possible to fully utilize the whole period of diastole so as to produce the longest possible disatolic augmentation. That is the increase of diatolic pressure due to externally applied pressure. Therefore, one measurement of effective counterpulsation is the ability to minimize systolic pressure, and at the same time maximize the ratio of the area under the disatolic wave form to that of the area under the systolic wave form. This consideration can be used to provide a guiding rule for determination of optimal deflation time.

Furthermore, the various existing external counterpulsation apparatuses only measure the electrocardiograph signals of the patient to guard against arrhythmia. Since counterpulsation applies pressure on the limits during diastole, which increases the arterial pressure in diastole and makes it higher than the systolic pressure, the blood flow dynamics and physiological parameters of the human body may vary significantly. Some of these variations may be advantageous, while some of them are potentially unsafe. For patients with arteriosclerosis and phelbosclerosis, there is the danger of blood vessels breaking due to the increase in their internal pressure. Furthermore, applying pressure to the limbs presses not only on the arteries but also the veins, and this may result in an increase in the amount of blood returning to the heart. This may cause cardiac lung or pulmonary edema because of the degration of the the decrease in pumping capacity of the heart and incapability of the heart to pump out the increased amount of blood returning to the heart. This may, in turn, affect the oxygen saturation in the arteries of the body and cause an oxygen debt. It is, therefore necessary to monitor the maximum value of the arterial pressure and oxygen saturation in the blood of a patient in addition to monitoring the electro-cardiogram, to ensure safetly of the patient during the counterpulsation treatment.

Furthermore, the gas distribution device in the existing external counterpulsation apparatuses operate by controlling the opening the closing of the solenoid valves, which has the disadvantage of having voluminous and complex pipe connections. This is disadvantageous to miniaturizing the whole apparatus and improving its portability.

SUMMARY OF THE INVENTION

Accordingly, it is an object of the present invention to overcome the above disadvantages and provide an improved efficiency external counterpulsation apparatus.

It is another object of the present invention to provide an external counterpulsation apparatus having accurate and reliable timing of inflation and deflation and reduced temperature of the pressurized gas, such that the gas flow temperature of the balloons is near to room temperature.

It is a further object of the present invention to provide a miniature external counterpulsation apparatus having a new gas distribution means and reduced pipe connections.

It is yet another object of the present invention to provide an external counterpulsation apparatus having devices for monitoring the blood pressure and oxygen saturation in the blood of a patient, and to monitor other complications arising from the treatment.

It is yet another object of the present invention to provide a negative suction to the deflation of the balloons so as to effectively exhaust all pressurized gas rapidly, to lower the systolic pressure, and reduce the noise level of the solenoid valves.

It is yet another object of the present invention to provide a semi-rigid or rigid balloon cuff which can either be molded into the shape of the surrounded limb, or used in conjunction with inserts of suitable incompressible materials; and used to occupy the dead space between the balloon cuff and surrounded limb to effectively reduce the volume of compressed gas and power loss as well as the time required to raise the external pressure to the required level for compression of the underlying vasculature.

It is a further object of the present invention to provide a more effeicient compressor for the use of external counterpulsation to produce the right volume of gas as the appropriate pressure, and which has reduced size, noise level and electrical power consumption.

To achieve the above objects of the invention, the present invention proposes an external counterpulsation apparatus, which comprises:

a first gas compressor;

a second gas compressor;

a control means;

a first positive pressure reservoir;

a second positive pressure reservoir;

a first negative pressure reservoir;

a second negative pressure reservoir;

a first solenoid valve;

a second solenoid valve;

a plurality of balloon devices, each of the balloon devices consisting of a balloon and a balloon cuff body which is made of a material of certain toughness and hardness, and fixing elements, wherein the shape of the balloon cuff body substantially matches the contour of the upper or lower limbs or the buttocks of the body;

a gas distribution means, comprising a cylinder and corresponding piston; a partition in the cylinder having a central hole therein which divides the cylinder into two portions, the piston also being divided into two portions, a first portion and a second portion, positioned one of each side of the partition, the two portions being connected by a rod passing through the central hole of the partition; a plurality of vents corresponding to said plurality of balloon devices which are symetrically arranged on two sides of a first portion of the cylinder, each of the vents being connected to a corresponding one of the plurality of balloons of the balloon devices by pipes; an outlet in this portion of the cylinder, which is connected to the first negative pressure reservoir by a pipe and to the second negative pressure reservoir via the second solenoid valve; the second portion of the piston is of an "I" shape and forms a cylindrical gas chamber within the cylinder, the axial length of the gas chamber being selected so that it communicates with each one of the symetrically arranged vents as the piston moves towards the first portion of the cylinder; a first vent, a second vent in the second portion and a third vent in the first portion of the cylinder, wherein the first vent is connected to the first solenoid valve by a pipe, the piston being movable towards the first portion of the cylinder when gas is flowing from the first positive pressure reservoir into the cylinder via the first solenoid valve, the second vent being positioned between the first portion of the piston and the partition and also being connected to the first solenoid valve by a pipe so that gas may flow from the first positive pressure reservoir into the gas chamber and move the piston in the opposite direction towards the second portion of the cylinder; the position of the third vent is selected such that whatever position in piston is in, the vent will always communicate with the gas chamber formed by the second portion of the piston and the cylinder, the third vent is connected to the second positive pressure reservoir by a pipe; gas flow consequentially inflate the plurality of balloons via the plurality of corresponding vents in the first portion of the cylinder as the piston moves across the plurality of vents; the outlet in the first portion of the cylinder being connected to the negative pressure reservoir by a pipe; when the balloons deflate the second solenoid is opened, and the gas in the balloons is discharged into the second negative pressure reservoir while discharging into the first negative pressure reservoir;

a control means, including a plurality of detector electrodes positioned at predetermined places on the body, a high frequency constant current source, filter means for electrocardiographic and impedance signals, and a computer system consisting of a micro-computer and A/D convertors, the computer system operating to perform adaptive filtering of the impedance cardiograph, to obtain data for controlling the inflation and deflation time of the balloons, and to generate corresponding inflation and deflation signals; a drive circuit, responsive to said inflation and deflation signals, operating to automatically inflate and deflate the balloons, and to discharge the gas in the negative pressure reservoirs.

Preferably the counterpulsation apparatus of the present invention also comprises a blood pressure detector means, for monitoring the blood pressure of the patient during counterpulsation comprising; solenoid valves the throttle valve for inflating and deflating the cuffs, electromagnetic pressure transducers for sensing pressure inside the cuffs, electrophoto-transducers for measuring pulse wave the oxygen saturation of blood, and an amplifying and filtering processing circuit. The maximum pressure of the arterial pressure is monitored by a cuff occlusive indirect blood pressure measuring method. At the beginning of measurement, the inflating passage of the solenoid valve is opened, gas for pressurizing the lower limbs inflates the cuffs via pipes and solenoid valves. Pressure transducers monitor the pressure inside the cuffs. When the pressure rises to a certain value after occlusion of the arteries and the electrophoto-transducer can not detect the pulse wave, the solenoid valve opens the deflating passage and the gas in the cuffs slowly deflates via the solenoid valves and the throttle valves and the pressure inside the cuffs slowly drops. When the pressure inside the cuffs is equal to or slightly below the maximum pressure of the arteries (which is the systalic pressure before counterpulsation, and diastole counterpulsation pressure during counterpulsation) the occluded blood vessels are pushed open instantaneously and at that time, a rapidly varying pulse wave can be detected by the electrophoto transducer, which indicates the arrival of the maximum pressure of the arteries. The pressure detected by the pressure transducer at the time is the maximum pressure. The apparatus preferably also includes a blood oxygen detector means, for monitoring the oxygen saturation in the blood during counterpulsation by the use of pulse blood oxygen measuring method. The transducer for pulse blood oxygen measurement cooperates with the electrophoto-transducer for detecting pulse waves in blood pressure measurement, and after amplifying and filtering, processing the saturation of blood oxygen is obtained by analyzing and calculating of the waveform by the micro-processor. When the blood pressure exceeds a predetermined value, or the blood oxygen saturation goes below a predetermined value, the computer issues a signal to stop the counterpulsation.

In addition, the present invention provides a method for controlling the external counterpulsation apparatus, comprising the steps of:

(a) obtaining an impedance cardiograph during counterpulsation with stable waveform and the distance characteristics such as the closure of the aortic valves using a plurality of electrodes and self-adaptive filtering technology;

(b) performing self-adaptive filtering processing and detecting of the impedance cardiograph by the use of micro-computer to obtain the closing point of the aortic valves and the starting point of the counterpulsation wave. The proper inflation time of the balloon cuffs can then be accurately determined by moving the starting point of the counterpulsation wave to coincide with the aortic valves closing time. In case there is too much noise in the impedance cardiograph such that determination of the aortic valves closure is impossible, then the inflation will be set at the end of the T wave of the electrocardiogram or using the method described in U.S. Pat. No. 4,753,226.

(c) Using impedance cardiograph to detect the peak amplitude and duration of the systemic systolic blood pressure and the amplitude and duration of the pulse wave created by counterpulsation to calculate objective index such as the ratio of peak diastolic to peak systolic blood pressure as well as the ratio of the area under the systolic and diastolic pulse wave as indications of the hemodynamic effectiveness of counterpulsation; and (d) The ability to determine the ratio of the areas under the diastolic and systolic pulse waves provides means to adjust the deflation time in such a way as to maximize this ratio. However, the adjustment of of the deflation time in maximizing the reduction of the systolic blood pressure is more important than maximization of the ratio under the diastolic and systolic pulse wave; and (e) controlling the inflation and deflation times of the external counterpulsation apparatus with a computer Preferably, the method may also comprise the steps of:

(f) detecting the blood pressure state of the patient with a blood pressure detector means during counterpulsation to improve safety, and stopping counterpulsation when the blood pressure exceeds a predetermined value; and (g) detecting the blood oxygen saturation of the patient with a blood oxygen detector means during counterpulsation to improve safety, and stopping counterpulsation when the blood pressure exceeds a predetermined level.

The advantages of the present invention lie in reduced gas consumption and effective counterpulsation, thereby reducing the burden on the gas compressor. In addition, discomfort or pain to the patient is reduced, and the burden on other environmental conditions is reduced as well, while the portability of the counterpulsation apparatus can be increased. Another significant advantage of the present invention lies in the non-invasive detection of the maximum arterial pressure and oxygen saturation of the blood of the patient, thereby guaranteeing the safety of the patient during counterpulsation treatment. And, more importantly, new control means and methods are adopted by the present invention, which make the inflation and deflation times of the counterpulsation apparatus more accurate and reliable, and improve the safety levels of counterpulsation treatment.

The above and other advantages of the present invention will be better appreciated with reference to the accompanying drawings and description of the preferred embodiments.

BRIEF DESCRIPTION OF THE DRAWINGS

FIG. 1 is a block diagram of a first embodiment of the external counterpulsation apparatus according to the present invention;

FIG. 2 is a block diagram of a second embodiment of the external counterpulsation apparatus according to the present invention;

FIG. 3 is a block diagram of a third embodiment of the external counterpulsation apparatus according to the present invention;

FIGS. 4A and 4B are detailed block diagrams of the control means in the external counterpulsation apparatus according to the present invention;

FIG. 4C is a detailed block diagram of the blood pressure and blood oxygen monitoring means illustrated in FIG. 4B;

FIG. 4D is a schematic diagram showing the relationships between the variation of cuff pressure, finger pulse wave, and opening and closing of the aortic valve;

FIGS. 5A and 5B are partial schematic diagrams of the gas source portion in the external counterpulsation apparatus according to the present invention, illustrating gas pipes connected to a semiconductor cooling device and air-conditioner cooling evaporator, respectively;

FIG. 6 is a schematic diagram of the balloon device used in the external counterpulsation apparatus according to the present invention, illustrating an improved structure of the balloon cuff body; and FIG. 7 is a flow chart of the method for controlling the external counterpulsation apparatus according to the present invention.

DETAILED DESCRIPTION OF THE INVENTION (PREFERRED EMBODIMENTS)

A detailed description of the present invention follows with reference to the accompanying drawings in which like elements are indicated by like reference numerals.

FIG. 1 is the block diagram of a first embodiment of the external counterpulsation apparatus according to the present invention, wherein a control means 10 controls the gas compressor 20 and set of solenoid valves 24. The compressor can be of rotary vane type, piston type, diaphragm or blower type. However, the preferred embodiment would be a scroll type compressor as described in the Chinese Patent CN1030814A which essentially consists of two scroll basin with very narrow gaps between them; with one scroll basin adapted to rotate at a very high speed (3,000 rpm) while the other scroll basin remains stationary. The clenching of the scroll basins compresses the air radially inwardly toward the center and the compressed air comes out of the center shaft. The scroll type of compressor is more efficient in operation, more quiet and smaller in size than other types of compressors and therefore, is suitable for the external counterpulsation apparatus described hereof. During operation, the compressor 20 operates to produce pressurized gas which is sent into the positive pressure reservoir 22 via the cooling means 21. A pressure limiting valve 23 is provided on the reservoir 22, which keeps the internal pressure of the reservoir 22 constant. The opening and closing of the set of solenoid valves 24 is controlled by the inflation and deflation driving signals generated by the control means in accordance with the heart impedance blood flow graph of the human body. The set of solenoid valves 24 include a number of two-position, -three-way solenoid valves corresponding to the number of balloons 25. When a valve is in the first of the two positions, it inflates its balloon, when it is in the second of the two positions, it deflates its balloon, under control of the control means.

FIG. 2 illustrates a second embodiment of the external counterpulsation apparatus according to the present invention. In this embodiment, a control signal is first generated by the control means 10, then the compressor 20 operates to compress gas into the positive pressure reservoir 22 after being cooled by the cooling means 21. A pressure limiting valve 23 is provided on the positive pressure reservoir to keep its internal pressure constant. A negative pressure reservoir 26 connected to the inlet of the compressor 20 produces negative pressure. The control means 10 controls the opening and closing of the set of solenoid valves 24 by issuing inflating and deflating driving signals in accordance with the results of detection. Again, when the set of solenoid valves 24 are in the first position, they inflate the balloons 25, when they are in the second position, they deflate the balloons 25. The gas discharged from the balloons is discharged into the negative pressure reservoir 26 via the set of solenoid valves 24, and then returns to the compressor 20. As there may be leakage during the circulation of gas, which may affect the amount of gas output from the compressor, a pressure limiting valve 27 is provided to adjust the negative pressure in the negative pressure reservoir. When the negative pressure exceeds a certain value, the pressure limiting valve 27 is opened to inject a certain amount of gas into the reservoir 26.

FIG. 3 illustrates a third embodiment of the external counterpulsation apparatus according to the present invention; wherein the control means 10 generates control signals and the compressor 20 operates to produce two portions of pressurized gas, one portion of pressurized gas is sent to the positive pressure reservoir 29, while another is sent into the positive pressure reservoir 22 via the cooling means 21 and the throttle valve 28. The pressure limiting valve 23 is operative to adjust the pressure inside the reservoir 22. The reference numeral 30 indicates a two-position, -five-way solenoid valve or two two-position, -three-way solenoid valves, 31 indicates a mono-directional throttle valve, 35 indicates a cylindrical gas distribution means or cylinder, 37 is a partition and 36 indicates a piston. When an inflation driving signal is issued by the control means, the solenoid valve 30 opens to the first of the two positions, and the gas flow is introduced into the portion I of the cylinder from the reservoir 29 via the solenoid valve 30 and the throttle governor 31 to push the piston from a first end towards a second end of the cylinder. A space portion III is formed by the piston and the cylinder and is always in communication with the reservoir 22, and vents for the balloons 25 are situated in sequence in the cylinder, the balloons being sequentially inflated as the piston moves towards the second end of the cylinder. When a deflation signal is issued by the control means, the solenoid valve 30 is moved to its second position, and the gas in the reservoir 29 enters the portion II of the cylinder via the solenoid valve 30 to push the piston back to the first end of the cylinder. At that time, the gas in portion I is discharged via the solenoid valve 30, and the gas in the balloons is discharged to the negative pressure reservoir 26. In order to speed deflation, a solenoid valve 34 is also opened at the same time and the gas discharged from the balloons is discharged to both negative pressure reservoirs 26 and 33. Negative pressure reservoir 33 is kept at a negative pressure by the input portion of compressor 32. Discharged gas is also sent to the reservoir 22 by the output portion of compressor 32.

During the deflation phase, if the pressurized balloon is simply exhausted into the atmosphere, exhaustion of the balloon may not be completed, with the residual gas pressing on the tissue mass surrounded by the balloon cuffs, reducing the much needed vascular space in the body to receive the volume of blood ejected by the heart. This reduces the ability of counterpulsation to unload systolic blood pressure and reduces cardiace workload. The addition of negative pressure reservoirs 26, 33 serves to effectively and rapidly evacuate the pressurized gas in the balloons at the onset of systole, thereby ensuring complete absence of pressure on the lower extremities, enabling the vasculature which has been previously compressed and emptied during the distolic period to act as suction to help the heart to eject blood out and unload the systolic blood pressure. In addition, the equally important, the addition of the negative pressure. In addition, and equally important, the addition of the negative pressure reservoirs 26, 33 ensures the smooth operation of the solenoid valves and prevents the leakage of large volumes of pressurized gas exhausting into the atmosphere. This closed gas system reduces the escape of noises generated by the opening and closing of solenoid valves and movement of air.

Furthermore, during normal operation of external counterpulsation, there is always some leakage of compressed air from the balloon during the inflation period. In order to compensate for the leakage of air to ensure there is adequate air for the intake of the compressor 20 to produce air pressure in the rant of 5 to 15 psi, a leakage compensation means such as the use of a vacuum limiting valve, a vacuum pump or compressor or some combination thereof is provided. An example of the compensation means is a vacuum limiting valve 27 connected to the negative pressure reservoir 26, set at approximately negative 100 mm Hg. When the negative pressure reservoir is less that 100 mm Hg, the vacuum limiting valve is open and air is sucked into the reservoir to provide more air for the intake of the compressor 20.

Prior art in external counterpulsation make use of bulky, noisy and power consuming solenoid valves are normally closed to reduce the generation of heat in keeping them open. However, this situation would induce danger to the patient in case of power failure if compressed gas is trapped in the balloons.

This invention provides; a gas cylindrical distribution system 35 as shown in FIG. 3, using a syringe system in pushing a piston in one direction to produce sequential inflation of the balloons, with the balloons 25 (not shown) furthest from the heart being inflated first. The balloons openings are placed on both sides of the cylinder, connecting to the left and right limbs as well as buttock. The number of balloons can be 2 to 8 or more on each side. This is achieved by connecting the balloons furthest from the heart to the portion of the cylinder closest to the piston, as the piston 36 moves from left to right as shown in FIG. 3. This gas distribution system uses compressed air to move a piston back and forth along a cylindrical means, producing a quiet operation without the need of too much power as compared to the use of bulky, noisy and power consuming solenoid inflation and deflation valves, thereby eliminating one of the most noisy parts of the prior art external counterpulsation apparatus, and reducing substantially the consumption of electric power. More importantly, the solenoid valve 30 is a normally open valve of portion II of the cylinder 35, thereby connecting portion II to the positive pressure reservoir 29 in case of power failure, moving the piston to the left of FIG. 3, exposing all the balloons to the negative pressure reservoir, thereby deflating all balloons and reducing the possibility of inducing trauma to the patient.

FIGS. 4A and 4B are detailed block diagrams of the control means in the external counterpulsation apparatus according to the present invention. Using impedance cardiography as the control means in detecting blood flow in the great arteries, the precise closure of the aortic valves and the pulse wave generated by external counterpulsation pressure in the external counterpulsation apparatus according to the present invention, wherein the reference numberal 1 indicates electrodes. The locations and types of electrodes used are for illustrative purpose and shouldnot be considered as constraint to such design and configuration.

The detecting electrode 1 consists of five point electrodes placed in the positions shown in FIG. 4A, that is, electrode A positioned at the root of the left ear or mastoid, electrode D positioned at the xiphoid process, electrode B positioned at the lift edge of the left sternum below the clavicle and electrode C positioned at the lift edge of the left sternum between the fourth and fifth ribs. Electrodes A and D are both impedance current electrodes, high frequency constant current being applied to the body from these two electrodes. Electrodes B and C are both detector electrodes for measurement of the blood flow impedance signals which may be derived from blood flow in the great arteries in the thoracic space A reference electrode E is positioned in the left anterior of the 10th rib, the signal obtained between electrodes C and E will be used as the reference signal for measuring movement of the body, especially motion artifact produced during the application of external counterpulsation pressure. The location of the reference electrode E is not important but should be further away from the thoracic space.

Before the start of external counterpulsation treatment, high frequency constant current is applied to electrodes A and D, and blood flow impedance signals related to the blood flow in the great arteries in the thoracic space will be picked up by detector electrodes B and C; these blood flow impedance signals also contain a dip in the wave form indicating the closure of the aortic valves.

Because of the location of the reference electrodes pair C and E, the blood flow impedance signals detected between these electrodes will be much weaker than the signals detected by electrodes B and C. Upon initiation of external counterpulsation, there will be two additional signals detected by both pairs of detective electrodes B, C and reference electrodes C and E, they are the retrograde blood flow impedance signals produced by the counterpulsation pressure, and the motion artifact produced by the same. The signals from motion artifact will present themselves to both pairs of electrodes in approximately equal amptitudes, while the signals from counterpulsation will be larger in the reference electrodes than in the detector electrodes because of the location of the reference electrodes in closer proximity to the counterpulsation hemodynamic effects. Consequently, subtraction of reference impedance signals from the detector impedance signals will provide a fairly clean blood flow impedance signals containing the time of aortic valves closure as well as the retrograde flow from counterpulsation. This kind of signal processing is known as self-adaptive filtering processing. By adjusting the onset of the inflation of the balloons, the retrograde blood flow signals can be advanced or retreated to coincide with the aortic valves closure thereby providing optimal counterpulsation timing. In addition, the adjustment of the optimal timing can also be performed by computer.

A high frequency constant current source 2 consists of: a transistor oscillator, amplitude limiting amplifier, band-pass filter and voltage-current current convertor to obtain a stable high frequency and stable amplitude current which is applied to the body by electrode A to measure the impedance.

An amplifier-filter circuit 3 for the electro-cardiographic signal consists of: a low-pass differential amplifier and band-pass filter-amplifier, which amplifies and filters the electrocardiographic signals of the body obtained from electrodes B and C.

A heart impedance signal amplifier-filter circuit 4 and a reference impedance signal amplifier-filter circuit 5 for adaptive processing consist of a band-pass filter-amplifier, a detector, a low-pass filter, and a differential circuit, signal amplifier-filter circuits amplify and filter the heart impedance blood flow signals obtained from the electrodes B and C, and the adaptive processed impedance reference signals obtained from the electrodes C and E.

A computer system consists of a personal micro-computer 7 and an A/D convertor 6. The A/D convertor converts the electrocardiographic signals, heart impedance blood flow signals, and impedance reference signals into digital signals and inputs them into the computer. The computer display the waveform, detects the QRS wave of the electrocardiogram indicates the upper and lower limits of the pulse rate, performs adaptive processing of the impedance blood flow signals and the impedance reference signals, measures the waveform's characteristic points such as the aortic valves closure and end diastolic and systolic amplitudes, and controls the inflation and deflation time of the external counterpulsation apparatus through a drive circuit 8.

FIG. 4B is also a detailed block diagram of the control means in the external counterpulsation apparatus according to the present invention, wherein a blood-pressure and blood oxygen monitoring means 9 are further added to the basic system shown in FIG. 4A.

FIG. 4C is a schematic block diagram of the blood-pressure and blood oxygen monitoring means 9 indicated in FIG. 4B.

FIG. 4D is a schematic diagram showing the relationships between the pressure variation of the cuff, finger pulse wave, and the opening and closing of the aortic valve.

Referring to FIG. 4C, 22 indicates the reservoir of the counterpulsation apparatus, which inflates a cuff 13 via a pipe, throttle valve 14, and a passage in a solenoid valve 15. The solenoid valve is two-position, three-way valve controlled by the computer 7. The other passage of the solenoid valve is a discharging passage for the cuff, the discharge speed being controlled by the throttle valve 14. At the beginning of blood pressure measurement, the inflation passage of the solenoid valve 15 is opened, the pressurized gas in the reservoir 22 inflates the cuff 13 via the throttle valve 14 to a predetermined pressure value at which the arteries are blocked. When they are blocked, a finger pulse transducer 16 is unable to detect a pulse wave. The inflating passage of the solenoid valve 15 is closed and the deflating passage is opened, the gas in the cuff discharges slowly via the solenoid valve 15 and the throttle valve 14 and the pressure inside the cuff drops slowly as shown by curve "a" in FIG. 4D. When the pressure in the cuff is equal to or slightly lower than the maximum arterial pressure, as shown by curve "b" in FIG. 4D, (systolic pressure before counterpulsation, and diastolic counterpulsation pressure during counterpulsation), the blocked blood vessels are pushed open instantaneously. At that time, the finger pulse transducer 16 will detect a rapidly varying pulsewave as shown by curve "c" in FIG. 4D. This indicates the arrival of the maximum pressure of the artery. The pressure detected by a pressure transducer 12 at that time is the maximum arterial pressure. Referring to FIG. 4C, 11 indicates an amplifying processing circuit for the pressure signal, and 17 indicates an amplifying processing circuit for the pulse signal. The amplified pressure and pulse signals are collected and processed by the computer 7 for performing corresponding counterpulsation control and calculation of oxygen saturation of blood.

It is a physical law that when air is compressed, heart will be generated. In external counterpulsation, approximately 25 c. ft. of air is compressed to 5 to 15 psi pressure, generating a gas with a temperature reaching as high as 90–100° C., depending on the environment and efficiency of the compression means. When compressed gas with such a high temperature is sent to the balloons which are in close contact with the patient's skin, it will produce abrasion or burn to the skin, or at the least, an uncomfortable feeling to the patient. Therefore, it is essential in this invention to provide means to cool the compressed air. In general, any means of cooling can be utilitied in this invention, including exposure to the atmosphere of a long piece or coil of metal pipe connecting the compression means to the positive pressure reservoir, use of a fan to force air to blow through a coil of metal pipe carrying the heated gas, water-cooling such as that used in the radiator of an automobile, running water cooling, or air conditioner.

FIGS. 5A and 5B are partial schematic diagrams of the gas source portion in the external counterpulsation apparatus according to the present invention, illustrating the gas pipes connected to a semiconductor cooling device and an air conditioner cooling evaporator, respectively. 21 and 21' indicate a semiconductor cooling device and an air conditioner cooling evaporator, respectively, 39 indicates a transmitting pipe, 38 indicates fins and 40 indicates heat isolation materials.

Prior art external counterpulsation apparatus utilized materials such as vinyl, leather, cloth or canvas to make the balloon cuffs. These cuffs are wrapped tightly around the lower limbs with balloons put in between the cuffs and the body. When compressed gas is inflated into the balloons, the cuff will also expand and extend outward due to the elasticity and extensibility of its material, causing significant energy loss since a large portion of the compressed air serves to deform the cuff. More importantly, when compressed air is used to expand and extend the cuffs outwardly the pressure inside the balloons will not be built up quickly, reducing the rate of compression of the tissue mass and the underlying vasculature, causing a slower external counterpulsation pulse wave moving up the aorta. This reduces the effectiveness of counter pulsation in increasing the perfusion pressure to the coronary arteries and, therefore, the development of collateral circulations (i.e. a set of new vessels formed in the myocardium (heart) bypassing the blockages in the coronary arteries). Therefore, the present invention provides the use of rigid or semi-rigid materials with little or no extensibility and elasticity so that the introduction of compressed air into the balloons will not cause the deformation or expansion of the cuffs, thereby requiring less pressurized air and reducing energy loss. Furthermore, the use of rigid or semi-rigid materials in making the cuffs will result in rapid filling of the balloons, quicker compression of the surrounded tissue mass and therefore a steeper external counterpulsation leading pulse wave travelling retrogradedly up the aorta to the heart.

FIG. 6 is a schematic diagram of the balloon device 41 in the external counterpulsation apparatus according to the present invention. A balloon cuff semiconductor cooling device and an airconditioner cooling evaporator, respectively, 39 indicates a transmitting pipe, 38 indicates fins and 40 indicates heat isolation materials.

Prior art external counterpulsation apparatus utilized materials such as vinyl, leather, cloth or canvas to take the balloon cuffs. These cuffs are wrapped tightly around the lower limbs with balloons put in between the cuffs and the body. When compressed gas is inflated into the balloons, the cuff will also expand and extend outward due to the elasticity and extensibility of its material, causing significant energy loss since a large portion of the compressed air serves to deform the cuff. More importantly, when compressed air is used to expand and extend the cuffs outwardly the pressure inside the balloons will not be built up quickly, reducing the rate of compression of the tissue mass and the underlying vasculature, causing a slower external counterpulsation pulse wave moving up the aorta. This reduces the effectiveness of counterpulsation in increasing the perfusion pressure to the coronary arteries and, therefore, the development of collateral circulations (i.e. a set of new vessels formed in the myocardium (heart) bypassing the blockages in the coronary arteries). Therefore, the present invention provides the use of rigid or semi-rigid materials with little or no extensibility and elasticity so that the introduction of compressed air into the balloons will not cause the deformation or expansion of the cuffs, thereby requiring less pressurized air and reducing energy loss. Furthermore, the use of rigid or semi-rigid materials in making the cuffs will result in rapid filling of the balloons, quicker compression of the surrounded tissue mass and therefore a steeper external counterpulsation leading pulse wave travelling retrogradedly up the aorta to the heart.

FIG. 6 is a schematic diagram of the balloon device 41 in the external counterpulsation apparatus according to the present invention. A balloon cuff rubber), the former could form a pressure bearing surface which fits the contour of the pressure bearing portion of the body when it bears pressure; while the latter could meet the needs of patients of various bodily forms by simply moving the paddings upward or downward to avoid the need to provide balloon cuffs of various sizes. To prevent the skin of a patient from being chaffed, a result of vibrations produced during counterpulsation, the edges of the balloon cuff body should be smoothed, this could be done by slightly turning the edges outwardly, and also could be done by wrapping the edges with soft materials (e.g. cloth, sponge, etc.). The balloon cuff body could be made from a single piece of material, but for convenient operation, it is preferable that it be fabricated in separated pieces which are coupled together with hinges 42 to enable freely opening and closing.

A balloon cuff body of proper size is selected or fitting paddings are inserted into the balloon cuff to fit the bodily form of the patient to make the balloon cuff closely encircle the corresponding portion of the patient. Fixing belts 45 are then tightened, and counterpulsation can begin.

FIG. 7 is a flow chart of the control method of the external counterpulsation apparatus according to the present invention, which comprises the steps of: a). obtaining an impedance cardiograph and electrocardiographic signals having a clear and stable wave form in the counterpulsation state by the use of detector electrodes 1, high frequency constant current source 2, and electrocardiographic and impedance signal amplifier-filter means 3, 4 and 5, which are collected and displayed by the computer system 7 (101); b). the computer system detecting the QRS wave of the electrocardiograph signal (102), performing adaptive processing of the impedance blood flow signal (103), obtaining the starting point of the counterpulsation blood flow wave by detecting the impedance cardiograph after self adaptive filtering processing (104), and calculating the data for controlling the inflation and deflation time of the counterpulsation apparatus from the interval of the R wave of the electrocardiographic signal and the starting point of the counterpulsing bloodflow wave (105); c). obtaining an objective index reflecting the curative effect of counterpulsation by detecting the peak amplitude of the waveform and duration of the heart systolic wave and counterpulsing wave in the impedance cardiograph (106); and d). controlling the inflation and deflation of the external counterpulsation apparatus by the computer (107). For the safety of the patient during counterpulsation, the control method of the present invention further comprises the following steps; e). detecting the blood pressure state of the patient with a blood pressure detector means during counterpulsation (108); f). detecting the oxygen saturation of the blood of the patient with a blood oxygen detector during counterpulsation (109). If they detected blood pressure value exceeds a predetermined value, or the blood oxygen saturation goes below a predetermined value, then the computer will direct the apparatus to stop counterpulsation.

In general, the only serious complications from external counterpulsation treatment are pulmonary edema and cerebral hemorrhage. Pulmmonary edema may arise because a left ventricular (left heart) failure, and usually can be detected with a rapid drop in the oxygen saturation of the arterial blood, from a normal value of 95–98% to a value lower than 85–90%. The monitor of oxygen saturation is an extremely sensitive parameter for the detection of pulmonary congestion due to left heart failure. The oxygen saturation can be monitored with a pulse oximeter available commercially and commonly used in any operating room. The use of pulse oximetry as a noninvasive method to detect the complications of pulmonary congestion (edema) as well as left heart failure is a noval concept provided in the present invention. Furthermore, cerebral hemorrhage usually result from high arterial blood pressure (hypertension). Since an effective external counterpulsation can raise the peak diastolic pressure to 40 to 60 mm Hg above systolic blood pressure, it is important not only to measure the resting blood pressure of the patient before initiation of external counterpulsation (so that hypertension patients can be treated medically to reduce their blood pressure before counterpulsation treatment), but it is also important to monitor the peak arterial blood pressure during treatment to ensure the peak blood pressure will not rise more than 40 to 50 mm Hg above resting systolk pressure. The present invention provides a novel means to monitor the peak blood pressure effectively. Historically, it has been extremely difficult to measure blood pressure using any of the presently available measuring methods during external counterpulsation because of motion artifact as well as the noisy environment. The present invention provides a means to accurately determine the peak blood pressure, thereby producing a critical parameter in eliminating such dangerous complications as cerebral hemorrhage.

A closed loop control procedure is performed by the computer and is as follows: At the beginning of the counterpulsation, the computer automatically sets the balloon inflation time to be at the end of the T wave of the electrocardiograph. Due to the delay before the arrival of the counterpulsing wave at the aorta, the closing point of the aortic valve and the starting point of the counterpulsation wave can be detected from the heart impedance blood flow graph by the computer. The computer adjusts the inflation time of the counterpulsation apparatus according to the time difference between these two points to move the starting point of the counterpulsing wave gradually towards the closing point of the aorta. While gradually matching these two points, the computer also calculates the aorta closing time with the Bazett formula ($T_{QT}=K\sqrt{T_{RR}}$) because of the effect of counterpulsation on the automatic detecting of the closing point of the aorta. The time QT calculated with the Bazett formula is taken as the closing time of the aortic valve after the Q wave of the electrocardiograph has been detected. This makes the starting point of the counterpulsing wave fall into a range centered at the closing time of the aortic valve. In the procedure of gradually matching the two points, the detection of the starting point of the counterpulsing wave may be affected by blood expulsion from the heart and the variation of blood flow inside the chest. If so, the computer determines the time delay between the arrival of the counterpulsing wave at the central region of the aorta and its formation by a the pressurization of the lower limbs of the patient, by determining the time difference between the detected starting point of the counterpulsing wave and the inflation time. The computer adjusts the counterpulsation inflation time, such that the starting point of the counterpulsation formed after the time delay falls into a range centered at the closing time of the aortic valve. The computer keeps it in this range during counterpulsation, thereby performing loop control.

It should be understood that various modifications and substitutions of conditions of the present invention could be made by those skilled in the art without departing from the spirit of the present invention, the scope of which is defined by the attached claims.

What is claimed is:

1. An external counterpulsation apparatus for use with a patient, comprising:

balloon means adapted to be received about the lower extremities of the patient, said balloon means including a plurality of inflatable devices;

a source of compressed fluid;

fluid reservoir means connected to the source of compressed fluid for inflating said balloon means; and fluid distribution means connected to the fluid reservoir means for distributing said source of compressed fluid to said balloon means;

wherein the balloon means comprises at least one inner balloon and at least one outer balloon cuff body, wherein the balloon cuff body generally follows the contour of the lower extremities of the body of the patient, and the balloon is connected to the fluid distribution means.

2. Apparatus as in claim 1 which further comprises control means for controlling the fluid distribution means to achieve inflation and deflation of the balloon means, including first electrodes for applying a constant current to the body, second electrodes for detecting an impedance waveform relating to the patient's blood flow to determine the closure of the aortic valves, the control means instituting the inflation of the balloon means so that the counterpulsation blood pulse reaches the aortic valves just after they have closed.

3. Apparatus as in claim 1 which further comprises control means for controlling the fluid distribution means to achieve inflation and deflation of the balloon means, including means for detecting an impedance waveform relating to the patient's blood flow to determine the closure of the aortic valves, means for measuring an impedance artifact relating to motion of the patient during counterpulsation and for removing the motion artifact from the impedance waveform, the control means instituting the inflation of the balloon means so that the counterpulsation blood pulse reaches the aortic valves just after they have closed.

4. Apparatus as in claim 1 which further comprises control means for controlling the fluid distribution means to achieve inflation and deflation of the balloon means and blood pressure detector means for monitoring the blood pressure of the patient during counterpulsation, the control means communicating with the blood pressure detector means and including means for comparing the blood pressure during counterpulsation to predetermined value and terminating the counterpulsation if such value is attained.

5. Apparatus as in claim 4 which further comprises blood oxygen detector means for monitoring the blood oxygen saturation of the patient during counterpulsation, the control means communicating with the blood oxygen detector means and including means for comparing the blood oxygen saturation during counterpulsation if the blood oxygen saturation falls outside of the range.

6. Apparatus as in claim 1 in which the source of compressed fluid comprises a scroll type compressor.

7. Apparatus as in claim 1 which further comprises means for cooling the compressed fluid.

8. Apparatus as in claim 1 wherein the balloon cuff body is formed from material which is initially moldable to generally follow the contour of the lower extremities of the body and then capable of hardening to a substantially nonexpandable form prior to use.

9. Apparatus as in claim 1 wherein the balloon cuff body is formed from material which will not substantially expand upon inflation of the balloon.

10. Apparatus as in claim 1 which further comprises insertion means for placement within the balloon cuff body to minimize air space between the balloon cuff body and the lower extremities of the patient.

11. Apparatus as in claim 1 which further comprises control means for controlling the fluid distribution means to achieve inflation and deflation of the balloon means, including means for generating a waveform corresponding to the diastolic and systolic blood pressure of the patient and adjusting the time of deflation of the balloon means to maximize the area and amplitude of the diastolic waveform and minimize the area and amplitude of the systolic waveform during counterpulsation.

12. Apparatus as in claim 1 which further comprises control means for controlling the fluid distribution means to achieve inflation and deflation of the balloon means, including at least one positive pressure reservoir for use in inflating the balloon means and at least one negative pressure reservoir for use in deflating the balloon means, and means to accelerate the withdrawal of fluid from the balloon means during a last part of the deflation to achieve substantially complete emptying of fluid from the balloon means.

13. An external counterpulsation apparatus for use with a patient, comprising:

a source of compressed fluid;

fluid reservoir means connected to the source of compressed fluid;

fluid distribution means connected to the fluid reservoir means;

balloon means adapted to be received about the lower extremities of the patient and connected to the fluid distribution means; and control means for controlling the fluid distribution means to achieve inflation and deflation of the balloons means, including first electrodes for applying a constant current to the body, second electrodes for detecting an impedance waveform relating to the patient's blood flow to determine the closure of the aortic valves, the control means instituting the inflation of the balloon means so that the counterpulsation blood pulse reaches the aortic valves just after they have closed;

wherein the balloon means comprises at least one inner balloon and at least one outer balloon cuff body, wherein the balloon cuff body generally follows the contour of the lower extremities of the body of the patient, and the balloon is connected to the fluid distribution means.

14. Apparatus as in claim 13 in which the control means further comprises means for measuring an impedance artifact relating to motion of the patient during counterpulsation and for removing the motion artifact from the impedance waveform.

15. Apparatus as in claim 13 which further comprises blood pressure detector means for monitoring the blood pressure of the patient during counterpulsation, the control means communicating with the blood pressure detector means and including means for comparing the blood pressure during counterpulsation to a predetermined value and terminating the counterpulsation if such value is attained.

16. Apparatus as in claim 13 which further comprises blood oxygen detector means for monitoring the blood oxygen saturation of the patient during counterpulsation, the control means communicating with the blood oxygen detector means and including means for comparing the blood oxygen detector means and including means for comparing the blood oxygen saturation during counterpulsation to a predetermined range and terminating the counterpulsation if the blood oxygen saturation falls outside of the range.

17. Apparatus as in claim 13 in which the source of compressed fluid comprises a scroll type compressor.

18. Apparatus as in claim 13 which further comprises means for cooling the compressed fluid.

19. Apparatus as in claim 13 wherein the balloon cuff body is formed from material which is initially moldable to generally follow the contour of the lower extremities of the body and then capable of hardening to a substantially non-expandable form prior to use.

20. Apparatus as in claim 13 wherein the balloon cuff body is formed from material which will not substantially expand upon inflation of the balloon.

21. Apparatus as in claim 13 which further comprises insertion mean for placement within the balloon cuff body to minimize airspace between the balloon cuff body and the lower extremities of the patient.

22. An external counterpulsation apparatus for use with a patient, comprising:

a source of compressed fluid;

fluid reservoir means connected to the source of compressed fluid;

fluid distribution means connected to the fluid reservoir means;

a plurality of balloon means, each balloon means including an inner balloon and an outer balloon cuff body, wherein the balloon cuff bodies of the plurality of balloon means match the contour of the lower extremities of the body of the patient, and the plurality of balloons are connected to the fluid distribution means;

control means for controlling the fluid distribution means to achieve inflation and deflation of the balloons; and the balloon cuff bodies being formed from material which is initially moldable to match the contours of the lower extremities of the body and then capable of hardening to a substantially non-expandable from prior to use.

23. An external counterpulsation apparatus for use with a patient, comprising:

a source of compressed fluid;

fluid reservoir means connected to the source of compressed fluid;

fluid distribution means connected to the fluid reservoir means;

a plurality of balloon means, each balloon means including an inner balloon and an outer balloon cuff body, wherein the balloon cuff bodies of the plurality of balloon means match the contour of the lower extremities of the body of the patient, and the plurality of balloons are connected to the fluid distribution means;

control means for controlling the fluid distribution means to achieve inflation and deflation of the balloons; and the balloon cuff bodies being formed from material which is semirigid or rigid such that it will not substantially expand upon inflation of the balloons.

24. An external counterpulsation apparatus for use with a patient, comprising:

a source of compressed fluid;

fluid reservoir means connected to the source of compressed fluid;

fluid distribution means connected to the fluid reservoir means;

a plurality of balloon means, each balloon means including an inner balloon and an outer balloon cuff body, wherein the balloon cuff bodies of the plurality of balloon means match the contour of the lower extremities of the body of the patient, and the plurality of balloons are connected to the fluid distribution means;

control means for controlling the fluid distribution means to achieve inflation and deflation of the balloons; and insertion means for placement within the balloon cuff bodies to minimize air space between the balloon cuff bodies and the lower extremities of the patient.

* * * * *